United States Patent
Jegham et al.

Patent Number: 5,929,089
Date of Patent: Jul. 27, 1999

[54] 5-PHENYL-3-(PIPERIDIN-4-YL)-1,3,4-OXADIAZOL-2(3H)-ONE DERIVATIVES FOR USE AS 5-HT4 OR H3 RECEPTOR LIGANDS

[75] Inventors: Samir Jegham, Argenteuil; Alistair Lochead, Charenton; Frédéric Galli, La Celle Saint Cloud; Alain Nedelec, Colombes; Axelle Solignac, Paris; Laurence De Cruz, Joinville Le Pont, all of France

[73] Assignee: Synthelabo, Le Plessis Robinson, France

[21] Appl. No.: 09/068,390

[22] PCT Filed: Nov. 5, 1996

[86] PCT No.: PCT/FR96/01730
    § 371 Date: May 8, 1998
    § 102(e) Date: May 8, 1998

[87] PCT Pub. No.: WO97/17345
    PCT Pub. Date: May 15, 1997

[30] Foreign Application Priority Data

Nov. 9, 1995 [FR] France ................... 95 13252
Nov. 9, 1995 [FR] France ................... 95 13253
Mar. 4, 1996 [FR] France ................... 96 02663

[51] Int. Cl.$^6$ ............ A61K 31/445; C07D 413/14; C07D 413/04
[52] U.S. Cl. ................... 514/316; 514/326; 546/187; 546/209
[58] Field of Search ............ 546/209, 187; 514/326, 316

[56] References Cited

U.S. PATENT DOCUMENTS 5,580,885  12/1996  King et al. .................. 514/321

FOREIGN PATENT DOCUMENTS 6-157518  6/1994  Japan .

WO94/05654  3/1994  WIPO .

OTHER PUBLICATIONS

Chemical Abstract, vol. 121, No. 23, Abstract 280649k, 1994, p. 1035.

Primary Examiner—Patricia L. Morris
Attorney, Agent, or Firm—Jacobson, Price, Holman & Stern, PLLC

[57] ABSTRACT

Compounds corresponding to the general formula (I)

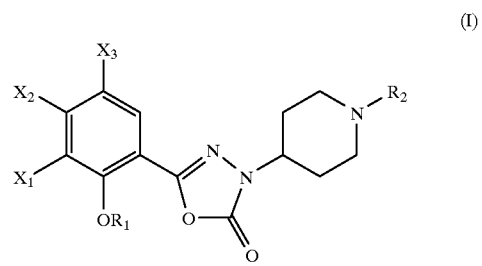

in which $R_1$ represents a $(C_1–C_4)$alkyl or $(C_3–C_7)$ cycloalkylmethyl group, $X_1$ represents a hydrogen or halogen atom or a $(C_1–C_4)$alkoxy group or else $OR_1$ and $X_1$ together represent a group of formula $-OCH_2O-$, $-O(CH_2)_2-$, $-O(CH_2)_3-$, $-O(CH_2)_2O-$ or $-O(CH_2)_3O-$, $X_2$ represents a hydrogen atom or an amino group, $X_3$ represents a hydrogen or halogen atom, and $R_2$ represents either a hydrogen atom or an optionally substituted $(C_1–C_6)$ alkyl group or a phenyl $(C_1–C_4)$ alkyl group which is optionally substituted on the phenyl ring or a phenyl $(C_2–C_3)$ alkenyl group or a phenoxy $(C_2–C_4)$ alkyl group or a cyclo $(C_3–C_7)$ alkylmethyl group or a 2,3-dihydro-1H-inden-1-yl or 2,3-dihydro-1H-inden-2-yl group or a group of general formula $-(CH_2)_n CO-Z$ in which n represents a number from 1 to 6 and Z represents a piperidin-1-yl or 4-(dimethylamino)piperidin-1-yl group. Application in therapeutics.

2 Claims, No Drawings

5-PHENYL-3-(PIPERIDIN-4-YL)-1,3,4-OXADIAZOL-2(3H)-ONE DERIVATIVES FOR USE AS 5-HT4 OR H3 RECEPTOR LIGANDS

5-Phenyl-3-(piperidin-4-yl)-1,3,4-oxadiazol-2(3H)-one derivatives, their preparation and their application in therapeutics.

The subject of the present invention is compounds corresponding to the general formula (I)

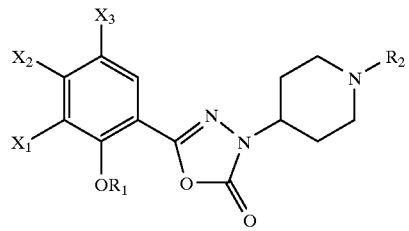

(I)

in which $R_1$ represents a $(C_1-C_4)$alkyl or $(C_3-C_7)$ cycloalkylmethyl group, $X_1$ represents a hydrogen or halogen atom or a $(C_1-C_4)$alkoxy group or else $OR_1$ and $X_1$ together represent a group of formula -OCH$_2$O-, -O(CH$_2$)$_2$-, -O(CH$_2$)$_3$-, -O(CH$_2$)$_2$O- or -O(CH$_2$)$_3$-, $X_2$ represents a hydrogen atom or an amino group, $X_3$ represents a hydrogen or halogen atom, and $R_2$ represents either a hydrogen atom or an optionally substituted $(C_1-C_6)$ alkyl group or a phenyl $(C_1-C_4)$ alkyl group which is optionally substituted on the phenyl ring or a phenyl $(C_2-C_3)$ alkenyl group or a phenoxy $(C_2-C_4)$ alkyl group or a cyclo $(C_3-C_7)$ alkylmethyl group or a 2,3-dihydro-1H-inden-1-yl or 2,3-dihydro-1H-inden-2-yl group or a group of general formula -(CH$_2$)$_n$CO-Z in which n represents a number from 1 to 6 and Z represents a piperidin-1-yl or 4- (dimethylamino)piperidin-1-yl group.

When $R_2$ represents an optionally substituted alkyl group, such a group is preferably a 2-ethoxy-2-oxoethyl group, a 2-(dimethylamino)-2-oxoethyl group, a 2-[(methylsulphonyl)amino]ethyl group, a 2-oxo-2-phenylethyl group, a 2-hydroxy-2-phenylethyl group, a butyl group, a 4,4,4-trifluorobutyl group or a 4-trifluoro-3-hydroxybutyl group.

When $R_2$ represents a phenyl $(C_1$ 14 $C_3)$ alkyl group which is optionally substituted on the phenyl ring, such a group is preferably a group optionally substituted on the phenyl ring by a halogen atom, by a trifluoromethyl group or by one or two methoxy groups.

When $R_2$ represents a group of general formula -(CH$_2$)$_n$CO-Z, such a group is preferably a 4-oxo-4-(piperidin-1-yl)butyl group, a 2-[4-(dimethylamino)piperidin-1-yl]-2-oxoethyl group, a 4-[4-(dimethylamino)piperidin-1-yl]-4-oxobutyl group, a 5-[4-(dimethylamino)piperidin-1-yl]-5-oxopentyl group or a 6-[4-(dimethylamino)piperidin-1-yl]-6-oxohexyl group.

The compounds of the invention can exist in the form of free bases or of addition salts with acids. Moreover, some $R_2$ substituents contain an asymmetric carbon atom; the compounds can therefore exist in the form of pure enantiomers or of mixtures of enantiomers.

In accordance with the invention, the compounds of general formula (I) can be prepared by a process illustrated in the following scheme.

Scheme

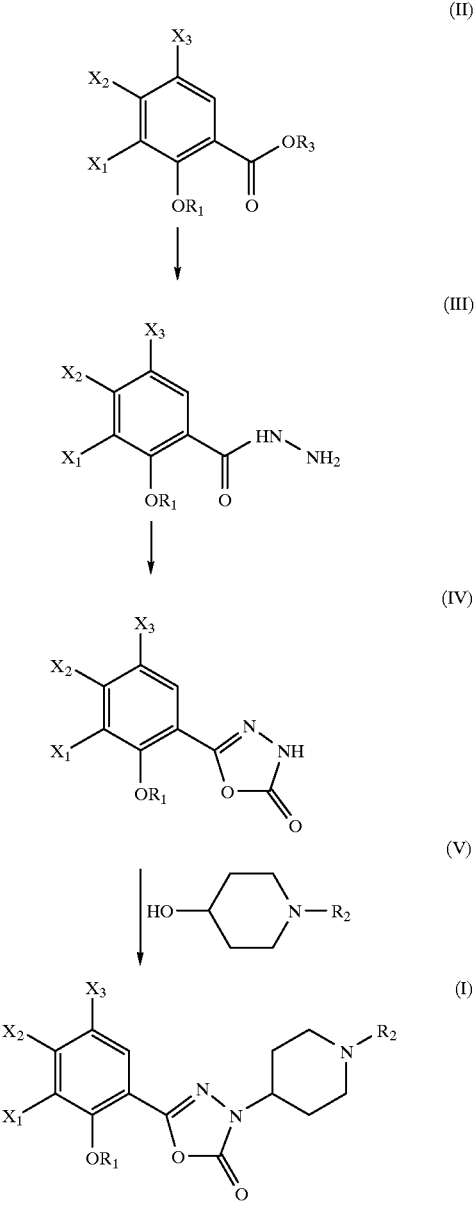

An ester of general formula (II), in which $R_1$, $X_1$, $X_2$ and $X_3$ are as defined above and $R_3$ represents a methyl or ethyl group, is reacted with hydrazine hydrate, in the absence of solvent or in a polar protic solvent, for example ethanol, in order to obtain a hydrazide of general formula (III), which is cyclized to the oxadiazole of general formula (IV), either by means of phosgene, in an aprotic solvent, for example dioxane, or by means of phenyl chloroformate, in an aprotic solvent, for example toluene. When, in the general formula (III), $X_2$ represents an amino group, the latter reacts with phosgene and the product obtained is esterified with benzyl alcohol, the amino group thus being protected by a benzyloxycarbonyl group. The oxadiazole of general formula (IV) is then reacted with a piperidin-4-ol of general formula (V), in which $R_2$ is as defined with respect to the general formula (I) but is other than a hydrogen atom or else represents a (1,1-dimethylethoxy)carbonyl protective group, in the presence of triphenylphosphine and ethyl azodicarboxylate, in an aprotic solvent, for example tetrahydrofuran, then, if it takes place, the nitrogen of the piperidine ring is deprotected by means of trifluoroacetic acid and, when $R_2$ represents a hydrogen atom and if it is desired, the compound obtained is reacted with a derivative of general formula $R_2$-X, in which X represents a leaving or functionalizable group, for example a halogen atom, a methanesulphonate or 4-methylbenzenesulphonate group or a carbonyl functional group, and $R_2$ is as defined with respect to the general formula (I) but is other than a hydrogen atom, in the presence of triethylamine, in an aprotic solvent, for example acetonitrile. In the specific case where $R_2$ represents a 2,3-dihydro-1H-indenyl group, a reductive amination is carried out with a compound of general formula (I) in which $R_2$ represents a hydrogen atom and the corresponding indanone.

The starting esters of general formula (II), or the corresponding acids, are known and described, in particular, in Patent Applications EP-0,231,139, EP-0,234,872, WO-8403281, WO-9316072 and WO-9419344.

The piperidin-4-ols of general formula (V) are known and/or can be prepared according to methods analogous to those described in *J. Mol. Pharmacol.,* (1992) 41(4), 718–726 and in Patent Applications WO-9303725 and EP-0,309,043.

The preparation of some compounds according to the invention is illustrated in detail in the following examples. The elemental microanalyses and the IR and NMR spectra confirm the structures of the compounds obtained. The numbers of the compounds shown in brackets in the titles correspond to those in the table given later. In the names of the compounds, the dash "-" forms part of the word and the dash "" is only used for the break at the line end; it is to be omitted in the absence of a break and must not be replaced by a normal dash or by a space.

EXAMPLE 1 (Compound No. 1).

5- (4-Amino-5-chloro-2-methoxyphenyl) -3- (piperidin-4-yl)-1,3,4-oxadiazol-2(3H)-one hydrobromide.

1.1. Hydrazide of 4-amino-5-chloro-2-methoxybenzoic acid.

51.5 g (0.239 mol) of methyl 4-amino-5-chloro-2-methoxybenzoate, in suspension in 460 ml of ethanol, are introduced into a 1 l reactor. 119 g (2.39 mol) of hydrazine hydrate are added over 15 min and the mixture is heated at reflux for 15 h. The mixture is cooled using an ice bath and the precipitate is collected by filtration, rinsed with ethanol and dried under reduced pressure at 80° C. for 2 h 30. 47.5 g of product are thus obtained. Melting point: 211° C.

1.2. Phenylmethyl [2-chloro-5-methoxy-4-(5-oxo-4,5-dihydro-1,3,4-oxadiazol-2-yl)phenyl]carbamate.

461 ml (0.875 mol) of a 1.93M solution of phosgene in toluene are added dropwise over the space of one hour, at room temperature and with magnetic stirring, to a suspension of 37.7 g (0.175 mol) of the hydrazide of 4-amino-5-chloro-2-methoxybenzoic acid in 1200 ml of dioxane in a 3 l reactor. The mixture is stirred at room temperature overnight and is then heated at 80° C. for 1 h. The excess phosgene is driven off by passing a stream of argon through at this temperature for 2 h. 72 ml (0.7 mol) of benzyl alcohol are then added and heating is continued for 1 h at 100° C. The mixture is cooled and concentrated under reduced pressure and the residue is triturated in isopropyl ether. The solid obtained is collected by filtration and dried. 60.3 g of product are thus obtained. Melting point: 214° C.

1.3. Phenylmethyl [2-chloro-4-[4-[1-[(1,1-dimethyl ethoxy)carbonyl]piperidin-4-yl]-5-oxo-4,5-dihydro-1,3,4-oxadiazol-2-yl]-5-methoxyphenyl]carbamate.

15.03 g (40 mmol) of phenylmethyl [2-chloro-5-methoxy-4-(5-oxo-4,5-dihydro-1,3,4-oxadiazol-2-yl)phenyl] carbamate, in solution in 200 ml of tetrahydrofuran, 13.64 g (52 mmol) of triphenylphosphine and 9.66 g of 1-[(1,1-dimethylethoxy)carbonyl]piperidin-4-ol are introduced into a 500 ml three-necked round-bottomed flask, while stirring the mixture at 0° C. 9.76 g (56 mmol) of ethyl azodicarboxylate are introduced and stirring is continued at 0° C. for 1 h and at room temperature for 2 h 30. The mixture is concentrated under reduced pressure, the residue is dissolved in ethyl acetate, the solution is washed a number of times with water and dried and the solvent is evaporated under reduced pressure. The residue is purified by chromatography on a column of silica gel, elution being carried out with a 30/70 mixture of ethyl acetate and hexane. 15 g of compound are obtained in the form of a white solid. Melting point: 140° C.

1.4. Phenylmethyl [2-chloro-4-(5-oxo-4-(piperidin-4-yl)-4,5-dihydro-1,3,4-oxadiazol-2-yl)-5-5 methoxyphenyl] carbamate.

6.52 g (12 mmol) of phenylmethyl [2-chloro-4-[4-[1-[(1,1-dimethylethoxy)carbonyl]piperidin-4-yl]-5-oxo-4,5-dihydro-1,3,4-oxadiazol-2-yl]-5-methoxyphenyl] carbamate, in solution in 140 ml of dichloromethane, and 13.64 g (120 mmol) of trifluoroacetic acid are introduced into a 500 ml three-necked round-bottomed flask and the mixture is stirred at room temperature overnight. Ice, then chloroform and then 25% aqueous ammonia are added, the organic phase is separated and the aqueous phase is extracted four times with chloroform. The organic phase is washed with a saturated aqueous sodium chloride solution and dried and the solvent is evaporated under reduced pressure. 6.26 g of crude compound are obtained, which compound is used as is. Melting point: 180° C.

1.5. 5-(4-Amino-5-chloro-2-methoxyphenyl)-3-(piperidin-4-yl)-1,3,4-oxadiazol-2(3H)-one hydrobromide.

1 g (2.8 mmol) of phenylmethyl [2-chloro-4-(5-oxo-4-(piperidin-4-yl)-4,5-dihydro-1,3,4-oxadiazol-2-yl)-5-methoxyphenyl]carbamate, dissolved in 5.8 ml of 33% hydrobromic acid in acetic acid, is placed in a 25 ml round-bottomed flask and the mixture is stirred at room temperature for 1 h. Diethyl ether is added and the precipitate is separated by filtration. 0.67 g of hydrobromide is obtained. Melting point: 278–280° C. By treatment with aqueous ammonia, 0.52 g of free base is recovered.

EXAMPLE 2 (Compound No. 5).

5-(4-Amino-5-chloro-2-methoxyphenyl)-3-[1-(cyclohexylmethyl)piperidin-4-yl]-1,3,4-oxadiazol-2(3H)-one.

2.01 ml (13.92 mmol) of triethylamine and then 0.92 g (5.2 mmol) of cyclohexylmethyl bromide in 5 ml of acetonitrile are successively added at room temperature, under an argon atmosphere and with magnetic stirring, to a solution of 1.13 g (3.48 mmol) of 5-(4-amino-5-chloro-2-methoxyphenyl)-3-(piperidin-4-yl)-1,3,4-oxadiazol-2(3H)-one in 40 ml of acetonitrile and the mixture is stirred at 70° C. for 2 days. The solvent is evaporated under reduced pressure, the residue is taken up in chloroform, the solution is washed a number of times with water and dried, the solvent is evaporated under reduced pressure and the residue is crystallized from acetone. 0.7 g of white solid is obtained. Melting point: 186.5–186.7° C.

EXAMPLE 3 (Compound No. 9).

5-(4-Amino-5-chloro-2-methoxyphenyl)-3-[1-(2-phenylethyl)piperidin-4-yl]-1,3,4-oxadiazol-2(3H)-one.

3.1. Phenylmethyl [2-chloro-5-methoxy-4-[5-oxo-4-[1-(2-phenylethyl)piperidin-4-yl]-4,5-dihydro-1,3,4-oxadiazol-2-yl]phenyl]carbamate.

1.84 g (4 mmol) of phenylmethyl [2-chloro-4-(5-oxo-4-(piperidin-4-yl)-4,5-dihydro-1,3,4-oxadiazol-2-yl)-5-methoxyphenyl]carbamate and 1.67 ml (12 mmol) of triethylamine, in suspension in 40 ml of acetonitrile, are placed in a 100 ml round-bottomed flask, 0.96 g (5.2 mmol) of (2-bromoethyl)benzene in 1 ml of acetonitrile is added, the mixture is heated at 60° C. for 3 h, a further 0.3 ml of (2-bromoethyl)benzene is added and the mixture is heated at 80° C. overnight. The solvent is evaporated under reduced pressure, the residue is extracted three times with chloroform, the organic phase is washed a number of times with water and is dried over sodium sulphate, the solvent is evaporated under reduced pressure and the residue is purified by chromatography on a column of silica gel, elution being carried out with an 80/20 mixture of ethyl acetate and hexane. 2.18 g of pure compound are obtained in the form of a white solid. Melting point: 150° C.

3.2. 5-(4-Amino-5-chloro-2-methoxyphenyl)-3-[1-(2-phenylethyl)piperidin-4-yl]-1,3,4-oxadiazol-2(3H)-one.

2.18 g (3.87 mmol) of phenylmethyl [2-chloro-5-methoxy-4-[5-oxo-4-[1-(2-phenylethyl)piperidin-4-yl]-4,5-dihydro-1,3,4-oxadiazol-2-yl]phenyl]carbamate, dissolved in 7 ml of a 33% solution of hydrobromic acid in acetic acid, are placed in a 100 ml round-bottomed flask and the mixture is stirred at room temperature for 3 h. Diethyl ether is added and the precipitate is isolated by filtration. 1.73 g of hydrobromide are obtained. The latter is taken up in water and chloroform and the mixture is neutralized by adding sodium hydroxide. After separation of the organic phase, extraction of the aqueous phase and the usual treatment, 1.44 g of compound are obtained in the form of the free base. Melting point: 184.5° C.

EXAMPLE 4 Compound No. 2).

5-(4-Amino-5-chloro-2-methoxyphenyl)-3-(1-methylpiperidin-4-yl)-1,3,4-oxadiazol-2(3H)-one hydrochloride.

4.1. Phenylmethyl [2-chloro-4-[4-(1-methylpiperidin-4-yl)-5-oxo-4,5-dihydro-1,3,4-oxadiazol-2-yl]-5-methoxyphenyl]carbamate.

7.5 g of phenylmethyl [2-chloro-5-methoxy-4-(5-oxo-4,5-dihydro-1,3,4-oxadiazol-2-yl)phenyl]carbamate, in suspension in 150 ml of tetrahydrofuran, 6.82 g (26 mmol) of triphenylphosphine and 2.3 g (20 mmol) of 1-methylpiperidin-4-ol are placed in a 2.5 l round-bottomed flask, 4.39 g (28 mmol) of ethyl azodicarboxylate are added at 0° C. and with magnetic stirring and the stirring is maintained for 20 h. The mixture is concentrated under reduced pressure, the residue is taken up in acetone and cooled to 0° C. and the precipitate is isolated by filtration. 5.02 g of compound are obtained in the form of a white solid. Melting point: 142° C.

4.2. 5-(4-Amino-5-chloro-2-methoxyphenyl)-3-(1-methylpiperidin-4-yl)-1,3,4-oxadiazol-2(3H)-one hydrochloride.

2 g (4.23 mmol) of phenylmethyl [2-chloro-4-[4-(1-methylpiperidin-4-yl)-5-oxo-4,5-dihydro-1,3,4-oxadiazol-2-yl]-5-methoxyphenyl]carbamate, dissolved in 20 ml of acetic acid, are placed in a 100 ml round-bottomed flask, 20 ml of 33% hydrobromic acid in acetic acid are slowly added and the mixture is stirred at room temperature for 18 h. Diethyl ether is added and the solid is isolated by filtration. 2 g of hydrobromide are obtained. It is dissolved in 30 ml of water, the solution is neutralized with sodium hydroxide and the precipitate is separated by filtration, washed with water and dried under reduced pressure. 1.05 g of compound are obtained in the form of the free base. Melting point: 162° C. The hydrochloride is obtained by treatment with hydrochloric acid in ethanol. Melting point: 212–218° C.

EXAMPLE 5 (Compound No. 19).

5-[4-Amino-5-chloro-2-(cyclopropylmethoxy)phenyl]-3-(1-butylpiperidin-4-yl)-1,3,4-oxadiazol-2(3H)-one hydrochloride.

5.1. Methyl 4-amino-5-chloro-2-(cyclopropylmethoxy)benzoate.

29.1 g (0.120 mol) of 4-amino-5-chloro-2-(cyclopropylmethoxy)benzoic acid and 340 ml of methanol are introduced into a 1 l three-necked round-bottomed flask, the solution is cooled to –40° C., 44 ml (0.602 mol) of thionyl chloride are added dropwise and the mixture is heated at reflux for 1 h 30. The mixture is cooled, the solvent is evaporated, the residue is taken up in water and an aqueous sodium carbonate solution, extraction is carried out with dichloromethane and the crude product is purified by chromatography on a column of silica gel, elution being carried out with a 90/10 to 80/20 mixture of n-heptane and ethyl acetate. 8.3 g of compound are obtained in the form of a pale-yellow solid. Melting point: 115° C.

5.2. Hydrazide of 4-amino-5-chloro-2-(cyclopropylmethoxy)benzoic acid.

6.0 g (23.5 mmol) of methyl 4-amino-5-chloro-2-(cyclopropylmethoxy)benzoate and 54 ml of ethanol are introduced into a 250 ml round-bottomed flask, 118 g (235 mmol) of hydrazine hydrate are added at 40° C. and the mixture is heated at reflux for 18 h. The mixture is cooled with an ice bath and the precipitate is isolated by filtration, rinsed with ethanol and dried under reduced pressure at 70° C. for 4 h. 4.7 g of compound are obtained. Melting point: 172° C.

5.3. 5-[4-Amino-5-chloro-2-(cyclopropylmethoxy)phenyl]-1,3,4-oxadiazol-2(3H)-one.

2.0 g (7.8 mmol) of the hydrazide of 4-amino-5-chloro-2-(cyclopropylmethoxy)benzoic acid, 17 ml of toluene and 1.9 ml (8.6 mmol) of phenyl chloroformate are introduced into a 100 ml round-bottomed flask and the mixture is heated at reflux for 4 h. The mixture is cooled to room temperature. 2.5 ml (16.4 mmol) of triethylamine are added, the mixture is heated at reflux for 3 h and cooled to room temperature, water is added and extraction is carried out with chloroform. After the usual treatment and purification by chromatography on a column of silica gel, elution being carried out with a 98/2/0.2 mixture of chloroform, methanol and aqueous ammonia, 0.80 g of white solid is obtained. Melting point: 153–154° C.

5.4. 5-[4-Amino-5-chloro-2-(cyclopropylmethoxy)phenyl]-3-(1-butylpiperidin-4-yl)-1,3,4-oxadiazol-2(3H)-one hydrochloride.

The final compound is obtained in the base form from 5-[4-amino-5-chloro-2-(cyclopropylmethoxy)phenyl]-1,3,4-oxadiazol-2(3H)-one and 1-butylpiperidin-4-ol, the preparation being carried out according to the method described in Example 4.1, and, after treatment with a solution of hydrochloric acid in ethanol and recrystallization from ethanol, the hydrochloride is obtained. Melting point: 237–238° C.

EXAMPLE 6 (Compound No. 28).

5-(8-Amino-7-chloro-2,3-dihydro-1,4-benzodioxin-5-yl)-3-(piperidin-4-yl)-1,3,4-oxadiazol-2(3H)-one hydrobromide.

6.1. Ethyl 8-amino-2,3-dihydro-1,4-benzodioxine-5-carboxylate.

23.5 g (0.198 mol) of thionyl chloride are slowly introduced into a 2 l three-necked round-bottomed flask containing 772 ml of ethanol cooled to −40° C., with stirring, stirring is maintained at this temperature for 1 h, 38.6 g (0.198 mol) of 8-amino-2,3-dihydro-1,4-benzodioxine-5-carboxylic acid, in solution in 100 ml of ethanol, are slowly added over 15 min and the mixture is allowed to return to room temperature overnight. The mixture is heated at reflux for 4 h, the solvent is evaporated under reduced pressure, the residue is taken up in water and sodium carbonate and extraction is carried out with chloroform. After washing, drying and evaporating the organic phase, 34.06 g of ester are obtained in the form of a white solid. Melting point: 112° C.

6.2. Ethyl 8-amino-7-chloro-2,3-dihydro-1,4-benzodioxine-5-carboxylate.

37 g (0.165 mol) of ethyl 8-amino-2,3-dihydro-1,4-benzodioxine-5-carboxylate, in solution in 370 ml of dioxane, are introduced into a 1 l round-bottomed flask, 23.2 g (0.174 mol) of N-chlorosuccinimide are added at room temperature and with magnetic stirring, and stirring is maintained overnight. The mixture is diluted with water, extraction is carried out with ethyl acetate and, after the usual treatment of the organic phase, 42 g of compound are obtained, which compound is recrystallized from a mixture of diethyl ether and diisopropyl ether. Melting point: 105–106° C.

6.3. Hydrazide of 8-amino-7-chloro-2,3-dihydro-1,4-benzodioxine-5-carboxylic acid.

38.4 g (0.149 mol) of ethyl 8-amino-7-chloro-2,3-dihydro-1,4-benzodioxine-5-carboxylate, in suspension in 150 ml of ethanol, are introduced into a 1 l reactor, 149 g (2.98 mol) of hydrazine hydrate are added over 15 min and the mixture is heated at reflux for 1 h. The mixture is cooled using an ice bath and the precipitate is collected by filtration, washed with ethanol and dried under reduced pressure. 33 g of compound are obtained. Melting point: 227–231° C.

6.4. Phenylmethyl [6-chloro-8-(5-oxo-4,5-dihydro-1,3,4-oxadiazol-2-yl)-2,3-dihydro-1,4-benzodioxin-5-yl] carbamate.

32.6 g of the hydrazide of 8-amino-7-chloro-2,3-dihydro-1,4-benzodioxine-5-carboxylic acid and 330 ml of dioxane are introduced into a 1 l reactor at room temperature and with magnetic stirring, 310 ml (0.4 mol) of a 0.193M solution of phosgene in toluene are added dropwise to this suspension over the space of one hour and a half, the mixture is stirred at room temperature overnight and is heated at reflux for 5 h.

The excess phosgene is driven off at this temperature by passing a stream of argon through for 2 h, the mixture is cooled and concentrated under r deduced pressure, the residue is taken up in 200 ml of benzyl alcohol and heated at 100° C. overnight, the mixture is cooled and concentrated under reduced pressure and the residue is triturated in diisopropyl ether. After filtering and drying, 52.6 g of compound are obtained. Melting point: 230° C.

6.5. Phenylmethyl [6-chloro-8-[4-[1-[(1,1-dimethylethoxy)carbonyl]piperidin-4-yl]-5-oxo-4,5-dihydro-1,3,4-oxadiazol-2-yl]-2,3-dihydro-1,4-benzodioxin-5-yl]carbamate.

8.07 g (20 mmol) of phenylmethyl [6-chloro-8-(5-oxo-4,5-dihydro-1,3,4-oxadiazol-2-yl)-2,3-dihydro-1,4-benzodioxin-5-yl]carbamate, 160 ml of tetrahydrofuran, 6.83 g (26 mmol) of triphenylphosphine, 4.83 g (24 mmol) of 1-[(1,1-dimethylethoxy)carbonyl]piperidin-4-ol and then 4.52 g (26 mmol) of ethyl azodicarboxylate are introduced, at 0° C. and with magnetic stirring, into a 250 ml three-necked round-bottomed flask. After stirring for 1 h at 0° C. and for 2 h 30 at room temperature, the mixture is concentrated under reduced pressure and the residue is recrystallized a first time from diethyl ether and a second time from ethyl acetate. 5.5 g of compound are obtained in the form of a white solid. Melting point: 206° C.

6.6. Phenylmethyl [6-chloro-8- (5-oxo-4- (piperidin-4-yl) -4,5-dihydro-1,3,4-oxadiazol-2-yl)-2,3-dihydro-1,4-benzodioxin-5-yl]carbamate.

5.3 g (9 mmol) of phenylmethyl [6-chloro-8-[4-[1-[(1,1-dimethylethoxy) carbonyl]piperidin-4-yl]-5-oxo-4,5-dihydro-1,3,4-oxadiazol-2-yl]-2,3-dihydro-1,4-benzodioxin-5-yl]carbamate, 100 ml of dichloromethane and 10.3 g (90 mmol) of trifluoroacetic acid are introduced into a 250 ml three-necked round-bottomed flask and the mixture is stirred at room temperature overnight. The mixture is concentrated under reduced pressure and the residue is triturated in acetone, collected by filtration, washed with diethyl ether, treated by slow addition of 17 ml of 25% aqueous ammonia and extracted four times with chloroform. After washing with water and then with a saturated sodium chloride solution, drying and evaporating the solvent, 4.4 g of compound are obtained, which compound is used as is in the following stage. Melting point: 128–130° C.

6.7. 5-(8-Amino-7-chloro-2,3-dihydro-1,4-benzodioxin-5-yl)-3-(piperidin-4-yl)-1,3,4-oxadiazol-2 (3H)-one 3.68 g (27.5 mmol) of phenylmethyl [6-chloro-8- (5-oxo-4-(piperidin-4-yl)-4,5-dihydro-1,3,4-oxadiazol-2-yl) -2,3-dihydro-1,4-benzodioxin-5-yl]carbamate and 35 ml of acetic acid are introduced into a 50 ml round-bottomed flask, 11 ml of 33% hydrobromic acid in acetic acid are added and the mixture is stirred at room temperature for 22 h. Diethyl ether is added to the precipitate which has formed and the precipitate is collected by filtration. 4 g of hydrobromide are obtained. Melting point >260° C. The compound is recovered in the form of the free base by treatment with sodium hydroxide. Melting point: 213–215° C.

EXAMPLE 7: (Compound No. 37)
5-(8-Amino-7-chloro-2,3-dihydro-1,4-benzodioxin-5-yl)-3-[1-[[4-(trifluoromethyl)phenyl]methyl]piperidin-4-yl]-1,3,4-oxadiazol-2(3H)-one.

1.58 ml (11.38 mmol) of triethylamine and 0.88 g (5.68 mmol) of 4-(trifluoromethyl)benzyl bromide, in solution in 5 ml of acetonitrile, are successively added at room temperature, with magnetic stirring and under an argon atmosphere, to a solution of 1 g (2.84 mmol) of 5-(8-amino-7-chloro-2,3-dihydro-1,4-benzodioxin-5-yl)-3-(piperidin-4-yl)-1,3,4-oxadiazol-2(3H)-one in 60 ml of acetonitrile and the mixture is stirred for 2 h. The solvent is evaporated under reduced pressure, the residue is taken up in chloroform, the solution is washed a number of times with water and dried and the solvent is evaporated under reduced pressure. The residue is crystallized from acetone and 1.14 g of white solid are obtained. Melting point: 198° C.

EXAMPLE 8 (Compound No. 32).
5- (8-Amino-7-chloro-2,3-dihydro-1,4-benzodioxin-5-yl)-3-[1-(4,4,4-trifluorobutyl)piperidin-4-yl]-1,3,4-oxadiazol-2 (3H)-one.

8.1. Phenylmethyl [6-chloro-8-[5-oxo-4-[1-(4,4,4-trifluorobutyl)piperidin-4-yl]-4,5-dihydro-1, 3,4-oxadiazol-2-yl]-2,3-dihydro-1,4-benzodioxin-5-yl] carbamate.

2 g (4.1 mmol) of phenylmethyl [6-chloro-8-(5-oxo-4-(piperidin-4-yl)-4,5-dihydro-1,3,4-oxadiazol-2-yl)-2,3- dihydro-1,4-benzodioxin-5-yl]carbamate, 40 ml of acetonitrile and 2.3 ml (16 mmol) of triethylamine are introduced into a 100 ml round-bottomed flask, 1.5 g (6.67 mmol) of 4,4,4-trifluorobutyl bromide in 1 ml of acetonitrile are added and the mixture is heated at 80° C. overnight. The solvent is evaporated under reduced pressure, the residue is extracted three times with chloroform and the organic phase is washed, dried and evaporated. After purification of the residue by chromatography on a column of silica gel, elution being carried out with a 97/3/0.3 mixture of dichloromethane, methanol and aqueous ammonia, 2.4 g of compound are obtained in the form of a white solid. Melting point: 158° C.

8.2. 5-(8-Amino-7-chloro-2,3-dihydro-1,4-benzodioxin-5-yl)-3-[1-(4,4,4-trifluorobutyl)piperidin-4-yl]-1,3,4-oxadiazol-2(3N)-one.

1.72 g (2.88 mmol) of phenylmethyl [6-chloro-8-[5-oxo-4-[1-(4,4,4-trifluorobutyl)piperidin-4-yl]-4,5-dihydro-1,3,4-oxadiazol-2-yl]-2,3-dihydro-1,4-benzodioxin-5-yl] carbamate and 17 ml of acetic acid are introduced into a 100 ml round-bottomed flask, 5 ml of 33% hydrobromic acid in acetic acid are added and the mixture is stirred at room temperature for 7 h. Diethyl ether is added to the precipitate which has formed and 1.8 g of hydrobromide are collected by filtration. It is taken up in water and chloroform, sodium hydroxide is added in order to release the base and, after the usual treatment of the organic phase, 1.19 g of compound are obtained. Melting point: 188° C.

EXAMPLE 9 (Compound No. 29).
5-(8-Amino-7-chloro-2,3-dihydro-1,4-benzodioxin-5-yl)-3-(1-methylpiperidin-4-yl)-1,3,4-oxadiazol-2(3H)-one hydrobromide.

9.1. Phenylmethyl [6-chloro-8-[4-(1-methylpiperidin-4-yl)-5-oxo-4,5-dihydro-1,3,4-oxadiazol-2-yl]-2,3-dihydro-1,4-benzodioxin-5-yl]carbamate.

6.27 g (15.53 mmol) of phenylmathyl [6-chloro-8-(5-oxo-4,5-dihydro-1,3,4-oxadiazol-2-yl)-2,3-dihydro-1,4-benzodioxin-5-yl]carbamate, in suspension in 80 ml of tetrahydrofuran, 6.12 g (23.3 mmol) of triphenylphosphine and 2.24 g (19.4 mmol) of 1-methylpiperidin-4-ol are introduced into a 250 ml round-bottomed flask and 4.06 ml (23.3 mmol) of ethyl azodicarboxylate are slowly added at 0° C. with stirring and the mixture is stirred for 48 h. The mixture is concentrated under reduced pressure, the residue is taken up in water, 1.6 ml of 37% hydrochloric acid and then 60 ml of ethyl acetate are added and the mixture is stirred for 1 h and then extracted four times with ethyl acetate. The solvent is evaporated under reduced pressure, the residue is treated with aqueous ammonia to pH=10 and the precipitate is collected by filtration. 3.16 g of compound are obtained in the form of a white solid. Melting point: 177° C.

9.2. 5-(8-Amino-7-chloro-2,3-dihydro-1,4-benzodioxin-5-yl)-3-(1-methylpiperidin-4-yl)-1,3,4-oxadiazol-2 (3H)-one hydrobromide.

1.71 g (3.41 mmol) of phenylmethyl [6-chloro-8-[4-(1-methylpiperidin-4-yl)-5-oxo-4,5-dihydro-1,3,4-oxadiazol-2-yl]-2,3-dihydro-1,4-benzodioxin-5-yl]carbamate, in solution in 30 ml of acetic acid, are introduced into a 100 ml round-bottomed flask, 3 ml of 33% hydrobromic acid in acetic acid are slowly added and the mixture is stirred for 5 h. Diethyl ether is added to the precipitate which has formed and the latter is collected by filtration. 1.72 g of hydrobromide are obtained. Melting point: 248° C.

EXAMPLE 10 (Compound No. 31).
5-(8-Amino-7-chloro-2,3-dihydro-1,4-benzodioxin-5-yl)-3-(1-butylpiperidin-4-yl)-1,3,4-oxadiazol-2(3H)-one hydrochloride.

10.1. Phenylmethyl [8-[4-(1-butylpiperidin-4-yl)-5-oxo-4,5-dihydro-1,3,4-oxadiazol-2-yl]-6-chloro-2,3-dihydro-1,4-benzodioxin-5-yl]carbamate.

The preparation is carried out as described in Example 9.1, from phenylmethyl [6-chloro-8-(5-oxo-4,5-dihydro-1,3,4-oxadiazol-2-yl) -2,3-dihydro-1,4-benzodioxin-5-yl] carbamate and 1-butylpiperidin-4-ol.

10.2. 5-(8-Amino-7-chloro-2,3-dihydro-1,4-benzodioxin-5-yl)-3-(1-butylpiperidin-4-yl)-1,3,4-oxadiazol-2(3H)-one hydrochloride.

The preparation is carried out as described in Example 9.2, from phenylmethyl [8-[4-(1-butylpiperidin-4-yl)-5-oxo-4,5-dihydro-1,3,4-oxadiazol-2-yl]-6-chloro-2,3-dihydro-1,4-benzodioxin-5-yl]carbamate and hydrobromic acid, and the hydrochloride is formed by treatment with hydrochloric acid in ethanol. Melting point: 280–283° C.

EXAMPLE 11 (Compound No. 62).
5-(5-Chloro-2,3-dihydrobenzofuran-7-yl) -3-(piperidin-4-yl)-1,3,4-oxadiazol-2(3H) -one hydrochloride.

11.1. Hydrazide of 5-chloro-2,3-dihydrobenzofuran-7-carboxylic acid.

57.3 ml (1.18 mol) of hydrazine hydrate are added to 25.14 g (0.118 mol) of methyl 5-chloro-2,3-dihydrobenzofuran-7-carboxylate in suspension in 300 ml of methanol and the mixture is heated at reflux for 4 h. The mixture is cooled using an ice bath and the precipitate is collected by filtration, washed with ethanol and dried under reduced pressure. 24.34 g of compound are obtained. Melting point: 182° C.

11.2. 5-(5-Chloro-2,3-dihydrobenzofuran-7-yl)-1,3,4-oxadiazol-2 (3H) -one.

24.34 g (0.115 mol) of the hydrazide of 5-chloro-2,3-dihydrobenzofuran-7-carboxylic acid and 500 ml of dioxane are introduced, at room temperature and with magnetic stirring, into a 1 l reactor, 178 ml (0.343 mol) of 0.193M phosgene in toluene are added by means of a dropping funnel and the mixture is stirred at room temperature for 24 h and then at reflux for 4 h in order to drive off the excess phosgene. The solvent is evaporated under reduced pressure and the residue is taken up in diethyl ether, collected by filtration and dried. 27 g of compound are obtained. Melting point: 270° C.

11.3. 5-(5-Chloro-2,3-dihydrobenzofuran-7-yl)-3-[1-[(1,1-dimethylethoxy)carbonyl]piperidin-4-yl]-1,3,4-oxadiazol-2(3H)-one.

20 g (0.08 mol) of 5-(5-chloro-2,3-dihydrobenzofuran-7-yl)-1,3,4-oxadiazol-2(3H)-one, in suspension in 250 ml of tetrahydrofuran, are introduced into a 500 ml three-necked round-bottomed flask, cooled to 0° C. and placed under magnetic stirring, followed by the addition of 10.06 g (0.05 mol) of 1-[(1,1-dimethylethoxy)carbonyl]piperidin-4-ol, 18.36 g of triphenylphosphine and 14.81 g (0.085 mol) of ethyl azodicarboxylate and the mixture is stirred at room temperature for 4 h. The mixture is concentrated under reduced pressure and the residue is recrystallized from a mixture of dichloromethane and diethyl ether. 14.7 g of beige solid are obtained. Melting point: 203° C.

11.4. 5-(5-Chloro-2,3-dihydrobenzofuran-7-yl)-3-(piperidin-4-yl)-1,3,4-oxadiazol-2(3H)-one hydrochloride.

14.7 g (0.035 mol) of 5-(5-chloro-2,3-dihydrobenzofuran-7-yl)-3-[1-[(1,1-dimethylethoxy)carbonyl]piperidin-4-yl]-1,3,4-oxadiazol-2(3H)-one are dissolved in 150 ml of dichloromethane in a 500 ml round-bottomed flask, 26.8 ml of trifluoroacetic acid are added at 0° C. and the mixture is stirred at room temperature for 3 h. 200 ml of water and 47 ml of 30% sodium hydroxide in 300 ml of water are added, the mixture is extracted with chloroform, the organic phase is dried and the solvent is evaporated under reduced pressure. 10.8 g of base are obtained in the form of a white solid. Melting point: 180° C. 3.5 g of hydrochloride are obtained by treatment of 5 g of base with a solution of gaseous hydrochloric acid in ethanol. Melting point: >260° C.

EXAMPLE 12 (Compound No. 67).
5-(5-Chloro-2,3-dihydrobenzofuran-7-yl)-3-[1-(2-phenylethyl)piperidin-4-yl]-1,3,4-oxadiazol-2(3H)-one hydrochloride.

2.5 g (7.77 mmol) of 5-(5-chloro-2,3-dihydrobenzofuran-7-yl)-3-(piperidin-4-yl)-1,3,4-oxadiazol-2(3H)-one, in solution in 50 ml of butan-2-one, are introduced into a 250 ml three-necked round-bottomed flask, 2.87 g (15.5 mmol) of phenylethyl bromide and then 2.36 g (23.3 mmol) of triethylamine are added and the mixture is stirred at reflux for 20 h. The precipitate formed is collected by filtration, the filtrate is evaporated under reduced pressure, the residue is taken up in water and extracted twice with chloroform and the organic phase is evaporated under reduced pressure. The residue is dissolved in a solution of gaseous hydrochloric acid in ethanol, diethyl ether is added and the precipitate is collected by filtration and recrystallized from ethanol. 2.0 g of hydrochloride are obtained. Melting point: 255–257° C.

EXAMPLE 13 (Compound No. 65).
5-(5-Chloro-2,3-dihydrobenzofuran-7-yl)-3-(1-butylpiperidin-4-yl)-1,3,4-oxadiazol-2(3H)-one.

2.38 g (0.01 mol) of 5-(5-chloro-2,3-dihydrobenzofuran-7-yl)-1,3,4-oxadiazol-2(3H)-one, in suspension in 80 ml of tetrahydrofuran, are introduced into a 250 ml three-necked round-bottomed flask, cooled to 0° C. and placed under magnetic stirring, 1.57 g (0.01 mol) of 1-butylpiperidin-4-ol, 3.41 g (0.013 mol) of triphenylphosphine and then 2.44 g (0.014 mol) of ethyl azodicarboxylate are added and the mixture is stirred at room temperature for 3 h and then at 40° C. for 3 h. The solvent is evaporated under reduced pressure and the residue is taken up in water and extracted five times with diethyl ether. The organic phase is dried over magnesium sulphate and filtered, the solvent is evaporated under reduced pressure and the residue is purified by chromatography on a column of silica gel, elution being carried out with an 80/20 mixture of ethyl acetate and heptane. 3 g of compound are obtained. Melting point: 133.8–134° C.

EXAMPLE 14 (Compound No. 71).
5-(6-Chloro-3,4-dihydro-2H-benzopyran-8-yl)-3-(piperidin-4-yl)-1,3,4-oxadiazol-2(3H)-one hydrochloride.

14.1. Hydrazide of 6-chloro-3,4-dihydro-2H-benzopyran-8-carboxylic acid.

72.8 ml (1.5 mol) of hydrazine hydrate are added to 34 g (0.15 mol) of methyl 6-chloro-3,4-dihydro-2H-benzopyran-8-carboxylate in solution in 250 ml of ethanol and the mixture is heated at reflux for 8 h. It is cooled using an ice bath and the precipitate is collected by filtration, washed with ethanol and dried under reduced pressure. 31 g of compound are obtained. Melting point: 149° C.

14.2. 5-(6-Chloro-3,4-dihydro-2H-benzopyran-8-yl)-1,3,4-oxadiazol-2(3H)-one.

31 g (0.137 mol) of the hydrazide of 6-chloro-3,4-dihydro-2H-benzopyran-8-carboxylic acid and 500 ml of dioxane are introduced, at room temperature and with magnetic stirring, into a 1 l reactor, 212.7 ml (0.411 mol) of 0.139M phosgene in toluene are added by means of a dropping funnel and the mixture is heated at reflux for 2 h. The precipitate is collected by filtration and dried. 26 g of compound are obtained. Melting point: 246° C.

14.3. 5-(6-Chloro-3,4-dihydro-2H-benzopyran-8-yl)-3-(piperidin-4-yl)-1,3,4-oxadiazol-2(3H)-one hydrochloride.

20 g (0.08 mol) of 5-(6-chloro-3,4-dihydro-2H-benzopyran-8-yl)-1,3,4-oxadiazol-2(3H)-one, in suspension in 300 ml of tetrahydrofuran, are introduced into a 500 ml three-necked round-bottomed flask, which has been cooled to 0° C. and placed under magnetic stirring, 15.94 g (0.08 mol) of 1-[(1,1-dimethylethoxy)carbonyl]piperidin-4-ol, 35.36 g (0.134 mol) of triphenylphosphine and 21.1 ml (0.134 mol) of ethyl azodicarboxylate are added and the mixture is stirred at room temperature for 4 h. The mixture is concentrated under reduced pressure, the residue is dissolved in 250 ml of dichloromethane, the solution is cooled to 0° C., 100 ml of trifluoroacetic acid are added and the mixture is stirred at room temperature for 2 h. It is concentrated under reduced pressure, 100 ml of a 1N aqueous hydrochloric acid solution are added and the precipitate is collected by filtration and dried. 19 g of hydrochloride are obtained. Melting point: 297° C.

EXAMPLE 15 (Compound No. 77).
5-(6-Chloro-3,4-dihydro-2H-benzopyran-8-yl)-3-[1-[4-[4-(dimethylamino)piperidin-1-yl]-4-oxobutyl]piperidin-4-yl]-1,3,4-oxadiazol-2(3H)-one hydrochloride.

1 g (2.68 mmol) of 5-(6-chloro-3,4-dihydro-2H-benzopyran-8-yl)-3-(piperidin-4-yl)-1,3,4-oxadiazol-2(3H)-one hydrochloride, in solution in 50 ml of acetonitrile, is introduced into a 250 ml three-necked round-bottomed flask, 1.24 ml (5.36 mmol) of 1-(4-chloro-1-oxobutyl)-N,N-dimethylpiperidin-4-amine and 1.12 ml (8 mmol) of triethylamine are added and the mixture is stirred at room temperature overnight. The mixture is evaporated under reduced pressure and the residue is taken up in water and extracted three times with chloroform. The organic phase is dried over magnesium sulphate and filtered, the solvent is evaporated under reduced pressure and the residue is purified by chromatography on a column of silica gel, elution being carried out with 98/2, 95/5 and then 90/10 mixtures of dichloromethane and methanol. A white solid is obtained which is treated in a solution of gaseous hydrochloric acid in ethanol and, after recrystallizing from ethanol, 0.22 g of hydrochloride is finally isolated. Melting point: 193° C.

EXAMPLE 16 (Compound No. 74).
5- (6-Chloro-3,4-dihydro-2H-benzopyran-8-yl) -3-[1-(1-methylethyl)piperidin-4-yl]-1,3,4-oxadiazol-2(3H)-one hydrochloride.

From 0.5 g (1.34 mmol) of 5-(6-chloro-3,4-dihydro-2H-benzopyran-8-yl)-3- (piperidin-4-yl) -1,3,4-oxadiazol-2 (3H)-one hydrochloride and 0.378 g (1.34 mmol) of 1-bromo-1-methylethane, and by carrying out the preparation as described in Example 15, 0.33 g of compound is obtained. Melting point: 241° C.

EXAMPLE 17 (Compound No. 81)
5-(6-Chloro-3,4-dihydro-2H-benzopyran-8-yl) -3-[1-(2,3-dihydro-1H-inden-2-yl)piperidin-4-yl]-1,3,4-oxadiazol-2 (3H)-one hydrochloride.

1.0 g (2.68 mmol) of 5-(6-chloro-3,4-dihydro-2H-benzopyran-8-yl) -3-(piperidin-4-yl) -1,3,4-oxadiazol-2 (3H)-one hydrochloride is added to a solution of 1.13 g (8.60 mmol) of indan-2-one in 15 ml of methanol containing 0.169 ml of acetic acid, 0.709 g (1.13 mmol) of sodium cyanoborohydride is added at a temperature of 5° C. and the mixture is stirred for 18 h. 15 ml of aqueous hydrochloric acid are added and, after stirring for 30 min, the mixture is neutralized with 2M aqueous sodium hydroxide. The mixture is extracted with dichloromethane, the organic phase is separated and dried and the solvent is evaporated under reduced pressure. The residue is purified by preparative thin layer chromatography, elution being carried out with a 98/2 mixture of dichloromethane and methanol. A white solid is obtained, the hydrochloride of which is prepared in the usual way. 0.8 g of salt is isolated. Melting point: 283–284° C.

EXAMPLE 18 (Compound No. 75)

5-(6-Chloro-3,4-dihydro-2H-benzopyran-8-yl)-3-[1-[5-[4-(dimethylamino)piperidin-1-yl]-5-oxopentyl]piperidin-4-yl]-1,3,4-oxadiazol-2(3H)-one fumarate (1:2).

A suspension of 2.0 g (5.37 mmol) of 5-(6-chloro-3,4-dihydro-2H-benzopyran-8-yl)-3-(piperidin-4-yl)-1,3,4-oxadiazol-2(3H)-one hydrochloride in 75 ml of acetonitrile containing 2.24 ml (16 mmol) of triethylamine and 1.44 g (5.37 mmol) of 1-(5-chloro-1-oxopentyl)-N,N-dimethylpiperidin-4-amine is heated at reflux for 2 h. 2.88 g (10.74 mmol) of additional 1-(5-chloro-1-oxopentyl)-N,N-dimethylpiperidin-4-amine are added and heating is continued for 18 h. The solvent is evaporated under reduced pressure and the residue is taken up in water and extracted with chloroform. After drying the organic phase, the residue is purified by chromatography on a column of silica gel, elution being carried out with a 98/2 to 90/10 mixture of dichloromethane and methanol. 0.4 g of product is obtained in the form of the base, the difumarate of which is prepared in the usual way. Melting point: 127° C.

The chemical structures and the physical properties of some compounds according to the invention are illustrated in the following table. In the $R_1$ and the $R_2$ columns, $cC_3H_5$ denotes a cyclopropyl group, $cC_6H_{11}$ a cyclohexyl group, $C_6H_5$ a phenyl group, $C_6C_4$-n-X a phenyl group substituted by X in the n-position, $C_6H_3$-m,n-$X_2$ a phenyl group disubstituted by X in the m-and n-positions, 1-$C_9H_9$ a 2,3-dihydro-1H-inden-1-yl group, 2-$C_9H_9$ a 2,3-dihydro-1H-inden-2-yl group, $NC_5H_{10}$ a piperidin-1-yl group and $NC_5H_9$-4-$N(CH_3)_2$ a 4-(dimethylamino)piperidin-1-yl group. In the Salt column, - denotes the base, HBr denotes a hydrobromide, HCl a hydrochloride, 2HCl a (1:2) hydrochloride, fum. a fumarate, 2fum. a (1:2) fumarate and tar. a tartrate. In the M.p. (°C.) column, (d) denotes a melting point with decomposition.

TABLE (I)

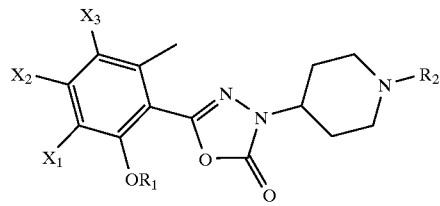

| No. | OR$_1$ | X$_1$ | X$_2$ | X$_3$ | R$_2$ | Salt | M.p.(° C.) |
|---|---|---|---|---|---|---|---|
| 1 | —OCH$_3$ | H | NH$_2$ | Cl | H | HBr | 278–280 |
| 2 | —OCH$_3$ | H | NH$_2$ | Cl | —CH$_3$ | — | 162 |
|   |   |   |   |   |   | HCl | 212–218 |
| 3 | —OCH$_3$ | H | NH$_2$ | Cl | —CH(CH$_3$)$_2$ | HCl | 248–251 |
| 4 | —OCH$_3$ | H | NH$_2$ | Cl | —(CH$_2$)$_3$CH$_3$ | HCl | 230 (d) |
| 5 | —OCH$_3$ | H | NH$_2$ | Cl | —CH$_2$cC$_6$H$_{11}$ | — | 186.5–186.7 |
| 6 | —OCH$_3$ | H | NH$_2$ | Cl | —(CH$_2$)$_2$CH(OH)CF$_3$ (R) | HCl | 226 |
| 7 | —OCH$_3$ | H | NH$_2$ | Cl | —CH$_2$C$_6$H$_5$ | HCl | 166 |
| 8 | —OCH$_3$ | H | NH$_2$ | Cl | —CH$_2$COC$_6$H$_5$ | — | 188.2 |
| 9 | —OCH$_3$ | H | NH$_2$ | Cl | —(CH$_2$)$_2$C$_6$H$_5$ | — | 184.5 |
| 10 | —OCH$_3$ | H | NH$_2$ | Cl | —(CH$_2$)$_3$C$_6$H$_5$ | — | 149.3–149.4 |
| 11 | —OCH$_3$ | H | NH$_2$ | Cl | —CH$_2$CH:CHC$_6$H$_5$ | — | 118.4–118.6 |
| 12 | —OCH$_3$ | H | NH$_2$ | Cl | —CH$_2$CO$_2$CH$_2$CH$_3$ | HCl | 223–224 |
| 13 | —OCH$_3$ | H | NH$_2$ | Cl | —CH$_2$CON(CH$_3$)$_2$ | HCl | 212–213 |
| 14 | —OCH$_3$ | H | NH$_2$ | Cl | —(CH$_2$)$_2$NHSO$_2$CH$_3$ | — | 167 |
| 15 | —OCH$_3$ | H | NH$_2$ | Cl | —(CH$_2$)$_3$CONC$_5$H$_9$-4-N(CH$_3$)$_2$ | — | 152 |
| 16 | —OCH$_3$ | H | NH$_2$ | Cl | —(CH$_2$)$_3$CONC$_5$H$_{10}$ | — | 209–211 |
| 17 | —OCH$_3$ | H | H | Cl | —(CH$_2$)$_3$CH$_3$ | — | 82.2–82.4 |
| 18 | —OCH$_3$ | H | H | Cl | —CH$_3$ | HCl | 255 |
| 19 | —OCH$_2$cC$_3$H$_5$ | H | NH$_2$ | Cl | —(CH$_2$)$_3$CH$_3$ | HCl | 237–238 |
| 20 | —OCH$_3$ | Cl | NH$_2$ | Cl | —(CH$_2$)$_3$CH$_3$ | HCl | 225–230 |
| 21 | —OCH$_3$ | H | NH$_2$ | Cl | —CH$_2$CH(OH)C$_6$H$_5$(±) | — | 200 |
| 22 | —OCH$_3$ | —OCH$_3$ | H | H | —(CH$_2$)$_2$C$_6$H$_5$ | HCl | 205 |
| 23 | —OCH$_3$ | H | NH$_2$ | H | —(CH$_2$)$_2$C$_6$H$_5$ | — | 181–182 |
| 24 | —OCH$_3$ | H | NH$_2$ | Cl | 2-C$_9$H$_9$ | HBr | 282–283 |
| 25 | —OCH$_3$ | H | NH$_2$ | Cl | 1-C$_9$H$_9$ | HCl | 207 |
| 26 | —OCH$_3$ | —OCH$_3$ | H | H | —(CH$_2$)$_4$CO—NC$_5$H$_9$-4-N(CH$_3$)$_2$ | fum. | 100–105 |
| 27 | —OCH$_3$ | H | NH$_2$ | Cl | —(CH$_2$)$_4$CO—NC$_5$H$_9$-4-N(CH$_3$)$_2$ | fum. | 180–182 |
| 28 | —O(CH$_2$)$_2$O— |  | NH$_2$ | Cl | H | — | 213–215 |
|   |   |   |   |   |   | HBr | >260 |
| 29 | —O(CH$_2$)$_2$O— |  | NH$_2$ | Cl | —CH$_3$ | HBr | 248 |
| 30 | —O(CH$_2$)$_2$O— |  | NH$_2$ | Cl | —CH(CH$_3$)$_2$ | — | 207 |
|   |   |   |   |   |   | HCl | 292–297 |
| 31 | —O(CH$_2$)$_2$O— |  | NH$_2$ | Cl | —(CH$_2$)$_3$CH$_3$ | — | 158–159 |
|   |   |   |   |   |   | HCl | 280–283 |

TABLE-continued

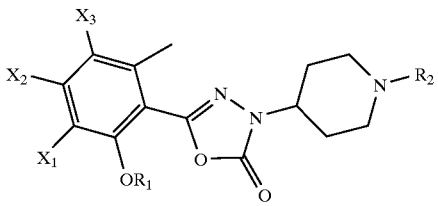

(I)

| No. | OR₁ | X₁ | X₂ | X₃ | R₂ | Salt | M.p.(° C.) |
|---|---|---|---|---|---|---|---|
| 32 | —O(CH₂)₂O— | NH₂ | | Cl | —(CH₂)₃CF₃ | — | 188 |
| 33 | —O(CH₂)₂O— | NH₂ | | Cl | —CH₂C₆H₅ | — | 198.3–199.9 |
| 34 | —O(CH₂)₂O— | NH₂ | | Cl | —(CH₂)₂C₆H₅ | HCl | 264.8–266.5 |
| 35 | —O(CH₂)₂O— | NH₂ | | Cl | —(CH₂)₃CO—NC₅H₉-4-N(CH₃)₂ | — | 165 |
| 36 | —O(CH₂)₂O— | H | | Cl | —(CH₂)₂C₆H₅ | — | 181.3–181.4 |
| 37 | —O(CH₂)₂O— | NH₂ | | Cl | —CH₂C₆H₄-4-CF₃ | — | 198 |
| 38 | —O(CH₂)₂O— | NH₂ | | Cl | —CH₂C₆H₄-4-F | HCl | 230–240 |
| 39 | —O(CH₂)₂O— | NH₂ | | Cl | —CH₂C₆H₄-4-OCH₃ | — | 171 |
| 40 | —O(CH₂)₂O— | H | | Cl | —(CH₂)₂C₆H₃-3,4-(OCH₃)₂ | — | 140 |
| 41 | —O(CH₂)₂O— | NH₂ | | Cl | —CH₂cC₃H₅ | — | 166 |
| 42 | —O(CH₂)₂O— | NH₂ | | Cl | —CH₂cC₆H₁₁ | — | 241 |
| 43 | —O(CH₂)₂O— | H | | Cl | —(CH₂)₃CH₃ | — | 122 |
| 44 | —O(CH₂)₂O— | H | | Cl | —(CH₂)₂C₆H₄-4-F | — | 173 |
| 45 | —O(CH₂)₂O— | H | | Cl | —(CH₂)₂C₆H₄-4-CF₃ | — | 134 |
| 46 | —O(CH₂)₂O— | NH₂ | | H | —CH₃ | — | 165 |
| 47 | —O(CH₂)₂O— | H | | H | —(CH₂)₃CH₃ | — | 104 |
| 48 | —O(CH₂)₂O— | H | | H | —(CH₂)₂C₆H₅ | HCl | 227–228 |
| 49 | —O(CH₂)₂O— | H | | H | H | HCl | >260 |
| 50 | —OCH₂O— | H | | H | —(CH₂)₂C₆H₅ | HCl | 225 (d) |
| 51 | —O(CH₂)₃O— | NH₂ | | Cl | —CH(CH₃)₂ | — | 151 |
| 52 | —O(CH₂)₃O— | NH₂ | | Cl | —(CH₂)₂C₆H₅ | HBr | 245 |
| 53 | —O(CH₂)₃O— | NH₂ | | Cl | —CH₂C₆H₅ | — | 160 |
| 54 | —O(CH₂)₃O— | NH₂ | | Cl | H | HBr | >340 |
| 55 | —O(CH₂)₃O— | NH₂ | | Cl | —(CH₂)₃CH₃ | — | 126 |
| 56 | —O(CH₂)₂O— | NH₂ | | Cl | (±) —CH₂CH(OH)C₆H₅ | — | 237 |
|  |  |  |  |  | (S) [α]$_D^{20}$ = +17.39, c = 1, DMSO | HCl | 240–245 |
|  |  |  |  |  | (R) [α]$_D^{20}$ = -17.3, c = 1, DMSO | HCl | 240–245 |
| 57 | —O(CH₂)₂O— | NH₂ | | Cl | —CH₂COC₆H₅ | — | 207 |
| 58 | —O(CH₂)₂O— | NH₂ | | Cl | —(CH₂)₃O—C₆H₄-4-F | HCl | 147 |
| 59 | —O(CH₂)₂O— | NH₂ | | Cl | —(CH₂)₄CO—NC₅H₉-4-N(CH₃)₂ | fum. | 128–132 |
| 60 | —O(CH₂)₂O— | H | | H | —(CH₂)₄CO—NC₅H₉-4-N(CH₃)₂ | fum. | 193–195 |
| 61 | —OCH₂O— | H | | H | —(CH₂)₄CO—NC₅H₉-4-N(CH₃)₂ | fum. | 217–220 |
| 62 | —O(CH₂)₂— | H | | Cl | H | HCl | >260 |
| 63 | —O(CH₂)₂— | H | | Cl | —CH₃ | HCl | 222 |
| 64 | —O(CH₂)₂— | H | | Cl | —CH(CH₃)₂ | HCl | 279 |
| 65 | —O(CH₂)₂— | H | | Cl | —(CH₂)₃CH₃ | — | 133.8–134 |
| 66 | —O(CH₂)₂— | H | | Cl | —CH₂C₆H₅ | HCl | 253–256 |
| 67 | —O(CH₂)₂— | H | | Cl | —(CH₂)₂C₆H₅ | HCl | 255–257 |
| 68 | —O(CH₂)₂— | H | | H | —(CH₂)₂C₆H₅ | HCl | 222 |
| 69 | —O(CH₂)₂— | H | | H | —(CH₂)₃CH₃ | — | (oil) |
| 70 | —O(CH₂)₃— | H | | Cl | —CH₂C₆H₅ | HCl | 259 |
| 71 | —O(CH₂)₃— | H | | Cl | H | HCl | 297 |
| 72 | —O(CH₂)₃— | H | | Cl | —(CH₂)₂C₆H₅ | HCl | 148 |
| 73 | —O(CH₂)₃— | H | | Cl | —(CH₂)₃CH₃ | HCl | 243 |
| 74 | —O(CH₂)₃— | H | | Cl | —CH(CH₃)₂ | HCl | 241 |
| 75 | —O(CH₂)₃— | H | | Cl | —(CH₂)₄CO—NC₅H₉-4-N(CH₃)₂ | 2fum. | 127 |
| 76 | —O(CH₂)₃— | H | | H | —(CH₂)₂C₆H₅ | HCl | 227 |
| 77 | —O(CH₂)₃— | H | | Cl | —(CH₂)₃CO—NC₅H₉-4-N(CH₃)₂ | HCl | 193 |
| 78 | —O(CH₂)₂— | H | | Cl | —(CH₂)₄CO—NC₅H₉-4-N(CH₃)₂ | fum. | 116–118 |
| 79 | —O(CH₂)₃— | H | | Cl | —CH₂CO—NC₅H₉-4-N(CH₃)₂ | tar. | 156–158 |
| 80 | —O(CH₂)₃— | H | | Cl | —(CH₂)₅CO—NC₅H₉-4-N(CH₃)₂ | tar. | 199–201 |
| 81 | —O(CH₂)₃— | H | | Cl | 2-C₉H₉ | HCl | 283–284 |
| 82 | —O(CH₂)₃— | H | | Cl | —(CH₂)₂CO—NC₅H₉-4-N(CH₃)₂ | tar. | 138–140 |

The compounds of the invention have formed the subject of tests which have demonstrated their advantage as substances possessing therapeutic activities.

Thus, the compounds of the invention were studied for their affinity with respect to 5-HT₄ receptors in the striatum of guinea pigs according to the method described by Grossman et al. in Br. J. Pharmacol., (1993) 109, 618–624. Guinea pigs (Hartley, Charles River, France) weighing 300 to 400 g are humanely killed, the brains are removed and the striata are excised and frozen at −80° C. On the day of the experiment, the tissue is defrosted at +4° C. in 33 volumes of HEPES-NaOH buffer (50 mM, pH=7.4 at 20° C.) and is homogenized using a Polytron® mill, the homogenate is centrifuged at 48,000 g for 10 min, the pellet is recovered, resuspended and recentrifigued under the same conditions and the final pellet is resuspended in REPES-NaOH buffer, in the proportion of 30 mg of tissue per ml. 100 μl of this membrane suspension are incubated at 0° C. for 120 min in the presence of [³H]GR113808 (ligand described in the cited article, specific activity 80–85 Ci/mmol) in a final volume of 1 ml of HEPES-NaOH buffer (50 mM, pH=7.4), in the presence or in the absence of test compound. Incubation is halted by filtration through a Whatman GF/B filter pretreated with 0.1% polyethyleneimine, each tube is rinsed with 4 ml of buffer at 0° C., filtration is again carried out and the radioactivity retained on the filter is measured by liquid scintigraphy. The non-specific binding is determined in the presence of 30 µM serotonin. The specific binding represents 90% of the total radioactivity recovered on the filter. For each concentration of studied compound, the percentage of inhibition of the specific binding of [³H]GR113808 and then the $IC_{50}$ the concentration of the tested compound which inhibits 50% of the specific binding, are determined. The $IC_{50}$ values of the most active compounds lie between 0.1 and 10 nM.

The compounds of the invention were also studied as regards their agonist or antagonist effects with respect to 5-HT$_4$ receptors in the rat oesophagus, according to the method described by Baxter et al. in *Naunyn Schmied. Arch. Pharmacol.*, (1991) 343, 439. Male Sprague-Dawley rats weighing from 300 to 450 g are used. An approximately 1.5 cm fragment is quickly removed from the end part of the oesophagus, the muscular layer is removed and the internal muscular mucosal tunic is opened longitudinally, mounted in an isolated organ vessel containing a Krebs-Henseleit solution at 32° C. oxygenated by a carbogen stream (95% $O_2$ and 5% $CO_2$) and connected to an isometric transducer under a basal tension of 0.5 g. A contraction of the tissue is induced by the addition of 0.5 µM of carbachol, there is a wait while the contraction becomes stabilized (15 min), and then the preparation is exposed to serotonin (1 µM) in order to quantify the maximum relaxation. The tissue is washed and, after a period of 20 min, 0.5 µM of carbachol is again added and the preparation is exposed to the study compound, in increasing additive concentrations from 0.1 to 1 µM. The compounds which induce a relaxation are regarded as 5-HT$_4$ agonists. For the compounds which do not induce relaxation, the preparation is exposed to serotonin in increasing additive concentrations, from 0.1 nM to a concentration inducing a maximum relaxation, and the relaxation curve due to serotonin, in the presence of the study compound, is then compared with a control curve prepared in the absence of the said compound. If its presence induces a shift of the curve towards the right, the study compound is then regarded as a 5-HT$_4$ antagonist.

The results of these two biological tests show that the compounds of the invention are powerful ligands for serotoninergic receptors of 5-HT$_4$ type and that they act on these receptors either as agonists or as antagonists.

Finally, the compounds of the invention have formed the subject of an in vitro study with respect to their affinity for the H$_3$ histaminergic receptors of the rat brain, essentially as described by Korte A. et al., *Biochem. Phys. Res. Commun.*, (1990) 168, 979–986, and West R. E. et al., *Mol. Pharmacol.*, (1990) 38, 610–613.

Male Sprague-Dawley rats (OFA, Iffa Credo, France), weighing from 250 to 300 g, are humanely killed and their brains are removed. The tissues are homogenized using a Polytron™ mill (position 7, for 20 s) in 20 volumes of Tris-HCl buffer (50 nM, pH 7.4 at 22° C.). The homogenate is centrifuged at 1000 g for 10 min and then the supernatant is subjected to a further centrifuging at 45,000 g for 20 min at 4° C. The pellet is then washed by resuspending in buffer, homogenizing and centrifuging. The final pellet is resuspended in the buffer in the proportion of 100 mg of starting tissue per milliliter and is then divided into 11 ml aliquot fractions which are frozen at −80° C. On the day of the experiment, the membrane suspension (100 µl, 300 to 400 µg of proteins) is incubated at 30° C. for 60 min in the presence of 0.5 nM of [³H]N$^\alpha$-methylhistamine (specific activity 75 to 80 Ci/mmol, New England Nuclear, Du Pont de Nemours, Boston, USA) in a final volume of 500 µl of Tris-HCl buffer, in the presence or in the absence of test compound. Incubation is halted by filtration through Whatman GF/B™ filters pretreated with polyethylenimine (0.4%). Each reaction tube is rinsed 3 times with 4 ml of cold (0° C.) Tris-HCl buffer. The filters are dried in an oven at 120° C. for 5 min. The radioactivity retained on the filters is determined by liquid scintigraphy. The non-specific binding is determined in the presence of 10 µM of thioperamide (N-cyclohexyl-4-(1H-imidazol-4-yl)piperidine-1-carbothioamide. For each concentration of studied compound, the percentage of inhibition of the specific binding of [³H]N$^\alpha$-methylhistamine is calculated and then the concentration $IC_{50}$ of compound which inhibits 50% of the binding is determined.

The most active compounds of the invention in this test have an $IC_{50}$ of the order of 5 nM.

The results of the various biological tests carried out on the compounds of the invention show that they are ligands for 5-HT$_4$ receptors and/or H$_3$ receptors. These results suggest that the compounds can be used for the treatment and prevention of disorders in which the 5-HT$_4$ and/or H$_3$ receptors are involved, in particular at the level of the central nervous system, of the gastrointestinal system, of the system of the lower urinary tract or of the cardiovascular system.

At the level of the central nervous system, these disorders and problems comprise in particular neurological and psychiatric disorders such as cognitive disorders, psychoses, compulsive and obsessional behaviours and states of depression and of anxiety. The cognitive disorders comprise, for example, memory and attention deficits, states of dementia (senile dementias of the Alzheimer's disease type or dementias related to age), cerebrovascular deficiencies or Parkinson's disease. The psychoses comprise, for example, paranoia, schizophrenia, mania and autism. The compulsive and obsessional behaviours comprise, for example, eating disorders of the loss of appetite or bulimia type. The states of depression and of anxiety comprise, for example, anxieties of anticipatory type (before a surgical operation, before dental treatment, and the like) or the anxiety caused by dependence on or withdrawal from alcohol or drugs. Finally, mention may also be made of mania, epilepsy, sleep disorders, seasonal affective disorders or migraines.

At the level of the gastrointestinal system, these disorders and problems comprise in particular direct or indirect disorders of gastromotility of the oesophagus, of the stomach or of the intestines, nausea or specific complaints, such as dyspepsia, ulcer, gastro-oesophagal reflux, flatulence, irritable bowel syndrome, disorders of intestinal secretion or diarrhoeas, for example those induced by cholera or by carcinoid syndrome, or disorders which may or may not be related to atmospheric pollution, such as asthma, rhinites and breathing difficulties.

At the level of the system of the lower urinary tract, these disorders and problems comprise in particular urinary incontinences, dysuria or urinary retention.

At the level of the cardiovascular system, these disorders and problems comprise in particular pathologies related, directly or indirectly, to cardiac arrhythmias, to hypertension, to ischaemia, to myocardial infarction or to unstable angina or problems of reocclusion after recanalization, for example after fibrinolytic or thrombolytic therapy, angioplasty or heart surgery. Glaucoma is also a disorder capable of being treated by the compounds of the invention.

The compounds of the invention can be presented in all forms of compositions appropriate for enteral or parenteral administration, such as tablets, dragées, capsules, including hard gelatin capsules, suspensions or solutions to be swallowed or injected, such as syrups or phials, and the like, in combination with suitable excipients, and in doses which make possible a daily administration of 0.001 to 20 mg/kg.

We claim:

1. Compound, optionally in the form of a pure optical isomer or of a mixture of such isomers, corresponding to the formula (I):

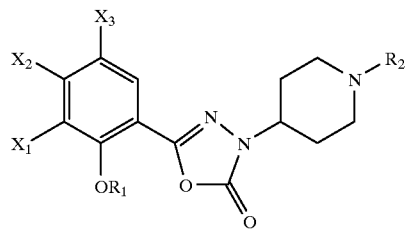

in which $R_1$ represents a $(C_1-C_4)$alkyl or $(C_3-C_7)$ cycloalkylmethyl group, $X_1$ represents a hydrogen or halogen atom or a $(C_1-C_4)$alkoxy group or $OR_1$ and $X_1$ together represent a group of formula $-OCH_2O-$, $-O(CH_2)_2-$, $-O(CH_2)_3-$, $-O(CH_2)_2O-$ or $-O(CH_2)_3O-$, $X_2$ represents a hydrogen atom or an amino group, $X_3$ represents a hydrogen or halogen atom, and $R_2$ represents a hydrogen atom, a 2-ethoxy-2-oxoethyl group, a 2-(dimethylamino)-2-oxoethyl group, a 2-[(methylsulphonyl)amino]ethyl group, a 2-oxo-2-phenylethyl group, a 2-hydroxy-2-phenylethyl group, a butyl group, a 4,4,4-trifluorobutyl group, a 4-trifluoro-3-hydroxybutyl group, a phenyl$(C_1-C_3)$alkyl group optionally substituted on the phenyl ring by a halogen atom, by a trifluoromethyl group or by one or two methoxy groups, a 4-oxo-4-(piperidin-1-yl)butyl group, a 2-[4-(dimethylamino)piperidin-1-yl]-2-oxoethyl group, a 4-[4-(dimethylamino)piperidin-1-yl]-4-oxobutyl group, a 5-[4-(dimethylamino)piperidin-1-yl]-5-oxopentyl group or a 6-[4-(dimethylamino)piperidin-1-yl]-6-oxohexyl group, in the form of the free base or of an addition salt with an acid.

2. Pharmaceutical composition, comprising a compound according to claim 1, in combination with an inert carrier.

* * * * *